(12) United States Patent
Robinson

(10) Patent No.: US 8,485,827 B1
(45) Date of Patent: Jul. 16, 2013

(54) SURGICAL ERROR PREVENTION SYSTEM

(76) Inventor: Cynthia Robinson, Goodyear, AZ (US)

( * ) Notice: Subject to any disclaimer, the term of this patent is extended or adjusted under 35 U.S.C. 154(b) by 212 days.

(21) Appl. No.: 12/784,562

(22) Filed: May 21, 2010

Related U.S. Application Data

(60) Provisional application No. 61/221,753, filed on Jun. 30, 2009.

(51) Int. Cl.
G09B 23/28 (2006.01)

(52) U.S. Cl.
USPC .......................................... 434/262; 434/267

(58) Field of Classification Search
USPC .................................................. 434/262, 267
See application file for complete search history.

(56) References Cited

U.S. PATENT DOCUMENTS

| | | | | |
|---|---|---|---|---|
| 3,698,383 A * | 10/1972 | Baucom | ....................... | 600/584 |
| 3,951,062 A * | 4/1976 | Abramson | .................... | 101/483 |
| 4,273,540 A * | 6/1981 | Dill | ............................... | 434/262 |
| 4,360,345 A * | 11/1982 | Hon | .............................. | 434/262 |
| 4,860,899 A * | 8/1989 | McKee | .......................... | 206/534 |
| 4,865,549 A * | 9/1989 | Sonsteby | ....................... | 434/262 |
| 4,926,885 A * | 5/1990 | Hinkle | .......................... | 128/898 |
| 4,947,867 A * | 8/1990 | Keeton | .......................... | 128/846 |
| 4,954,239 A * | 9/1990 | Mueller | ......................... | 206/571 |
| 5,102,169 A * | 4/1992 | Mayfield | ....................... | 283/115 |
| 5,163,557 A * | 11/1992 | Sokolowski | .................. | 206/439 |
| 5,261,702 A * | 11/1993 | Mayfield | ....................... | 283/115 |
| 5,356,295 A * | 10/1994 | Grosz | .......................... | 434/267 |
| 5,494,442 A * | 2/1996 | Hecht | ........................... | 434/267 |
| 5,498,034 A * | 3/1996 | Ford | ............................... | 283/67 |
| 5,636,873 A * | 6/1997 | Sonsteby | ........................ | 283/81 |
| 5,720,502 A * | 2/1998 | Cain | .............................. | 283/115 |
| 5,769,859 A * | 6/1998 | Dorsey | .......................... | 606/119 |
| 5,984,368 A * | 11/1999 | Cain | .............................. | 283/115 |
| 5,992,890 A * | 11/1999 | Simcox | ........................ | 283/66.1 |
| 6,155,603 A * | 12/2000 | Fox | ................................. | 283/62 |
| 7,107,547 B2 * | 9/2006 | Cule et al. | ..................... | 715/810 |
| 7,180,014 B2 * | 2/2007 | Farber et al. | ............... | 177/25.19 |
| 7,297,148 B2 | 11/2007 | Waxman | | |
| 7,461,079 B2 * | 12/2008 | Walker et al. | ......................... | 1/1 |
| 7,736,149 B2 * | 6/2010 | Towliat | ........................ | 434/267 |
| 2002/0179094 A1 * | 12/2002 | Perlow | .......................... | 128/897 |
| 2003/0182815 A1 * | 10/2003 | Carlson, II | ..................... | 33/566 |
| 2003/0184081 A1 * | 10/2003 | Carlson, II | ...................... | 283/67 |

(Continued)

OTHER PUBLICATIONS

Mitchell, Alfred. SURGI-COLOR GUARD. Feb. 3, 2009.*

Primary Examiner — Robert J Utama
(74) Attorney, Agent, or Firm — Kenneth L Tolar

(57) ABSTRACT

A system for preventing surgical site errors includes a ferromagnetic, dry-erase whiteboard having a pair of anatomical figures imprinted thereon. Adjacent to the anatomical figures is a text space for writing a description of a planned surgical procedure. The system further includes a plurality of color-coded magnets for securing to representative locations on the anatomical figures. Each magnet has a specific color according to the area of the body requiring surgery. A medical worker places a color-coded magnet on one of the whiteboard anatomical figures at a location corresponding to the planned surgical site. The worker writes a description of the surgical procedure on the text space using a colored marker(s) that matches the magnet color(s) and then covers the patient with an identically-colored surgical drape. A surgeon first examines the whiteboard to identify the magnet location and color, then examines the written description and color and finally examines the drape color. If all colors agree and correlate with the written description, surgery may safely begin; otherwise, the surgeon is alerted to investigate the discrepancy.

5 Claims, 2 Drawing Sheets

U.S. PATENT DOCUMENTS

| | | |
|---|---|---|
| 2004/0056478 A1* | 3/2004 | Bruce .............................. 283/81 |
| 2004/0194673 A1* | 10/2004 | Comeaux et al. ............... 108/90 |
| 2006/0078860 A1 | 4/2006 | Towliat |
| 2006/0095087 A1* | 5/2006 | Shin ................................ 607/46 |
| 2006/0149296 A1* | 7/2006 | Stanners ....................... 606/116 |
| 2007/0028344 A1* | 2/2007 | Czajka .............................. 2/51 |
| 2007/0136097 A1 | 6/2007 | Demers et al. |
| 2008/0270341 A1* | 10/2008 | Youngblood ..................... 707/1 |
| 2010/0082368 A1* | 4/2010 | Gecelter et al. ................... 705/3 |

* cited by examiner

US 8,485,827 B1

SURGICAL ERROR PREVENTION SYSTEM

CROSS REFERENCE TO RELATED APPLICATIONS

This application is entitled to the benefit of provisional application No. 61/221,753 filed on Jun. 30, 2009, the specification of which is incorporated herein by reference.

BACKGROUND OF THE INVENTION

The present invention relates to a system for preventing surgical site errors.

DESCRIPTION OF THE PRIOR ART

Although somewhat rare, surgical site errors cause numerous injuries and disabilities each year. Since most of the errors are attributable to fatigue, data misplacement or poor document control, they would be easily preventable if convenient safeguards were implemented. Accordingly, there is currently a need for a method of verifying proposed surgical sites to minimize errors.

A review of the prior art reveals several methods for preventing surgical errors. For example, U.S. published patent application no. 20060078860 filed on behalf of Towliat discloses a method for preventing surgical errors comprising a display having a START indicator and a STOP indicator, one of which is illuminated or otherwise highlighted to alert a surgeon to either proceed or refrain from surgery. The display includes a pair of anatomical figures thereon, one corresponding to the posterior portion of a human body and the other corresponding to the anterior portion. Individual sections of each figure can be highlighted to visually indicate a proposed surgical site.

U.S. published patent application no. 20070136097 filed on behalf of Demers et al. discloses a risk-reduction method for surgical procedures including the use of an internet server and an operating room display screen.

U.S. published patent application no. 20040056478 filed on behalf of Bruce discloses a surgical safety method including the use of markers or decals having either admonishing or permissive indicia thereon. A marker having the admonishing indicia is placed on the side of the patient that is not undergoing surgery while the marker having the permissive indicia is placed on the side undergoing surgery to prevent a surgeon from performing a "wrong side" surgery.

U.S. published patent application no. 20030182815 filed on behalf of Carlson, II discloses a surgical site marking system that includes placing an adhesive, incise material on a proposed surgical site and performing the surgery through the material. A surgical robe having an opening that is aligned with the incise material is placed on the patient whereby surgery is performed through both the opening and the material.

U.S. Pat. No. 7,297,148 issued to Waxman discloses surgical safety procedure including attaching a microchip to a patient at the anatomical location of the intended surgery.

As indicated above, several surgical-site error-prevention methods exist in the prior art. However, the conventional methods simply include either directly marking a pertinent area of a patient's body, or an anatomical depiction thereof, which can still result in a surgical error if a worker marks the wrong location. Accordingly, there is a need for a surgical error prevention system that includes additional safeguards to prevent incorrect identification of surgical sites. The present invention addresses this need by providing a method that employs color-coded magnets for attaching to anatomical figures that are compared with color-coded surgical drapes and written text to identify and verify a proposed surgical site.

SUMMARY OF THE INVENTION

A system for preventing surgical site errors includes a ferromagnetic, dry-erase whiteboard having a pair of anatomical figures imprinted thereon. Adjacent to the anatomical figures is a text space for writing a description of a planned surgical procedure. The system further includes a plurality of color-coded magnets for securing to representative locations on the anatomical figures. Each magnet has a specific color according to the area of the body requiring surgery. A medical worker places a color-coded magnet on one of the whiteboard anatomical figures at a location corresponding to the planned surgical site. The worker writes a description of the surgical procedure on the text space using a colored marker(s) that matches the magnet color(s), and then covers the patient with an identically-colored surgical drape. A surgeon examines the whiteboard to identify the magnet location and color, then examines the written data content and color and finally examines the drape color. If all colors agree, surgery may safely begin; otherwise, the surgeon is alerted to investigate the discrepancy.

It is therefore an object of the present invention to provide a method of minimizing surgical site errors.

It is another object of the present invention to provide a method that uses color-coded visual aids to verify a planned surgical site.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
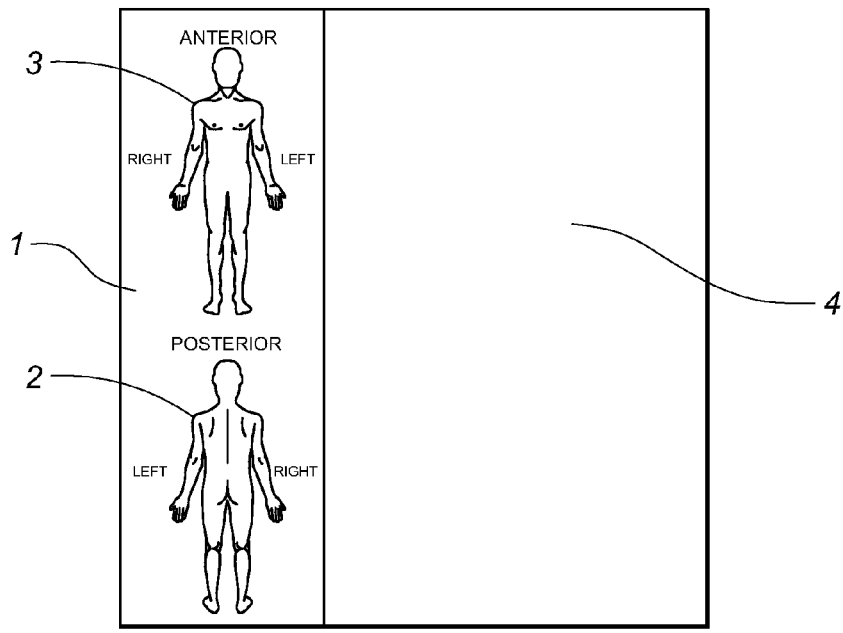
FIG. 1 is a front, plan view of the whiteboard according to the present invention.
Figure 2:
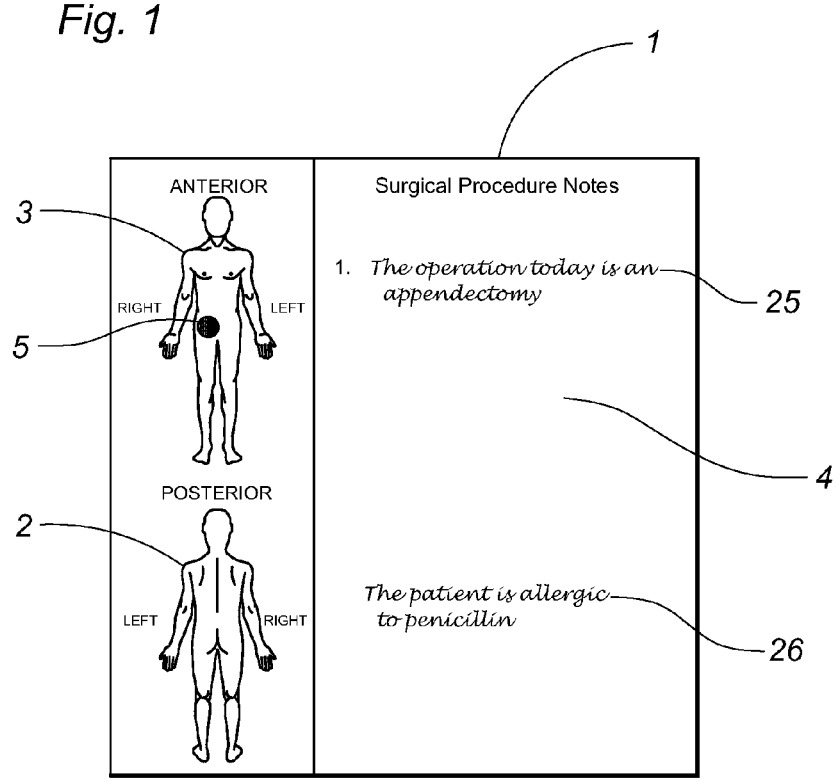
FIG. 2 depicts the whiteboard of FIG. 1 with a magnet secured to one of the anatomical figures.
Figure 3:
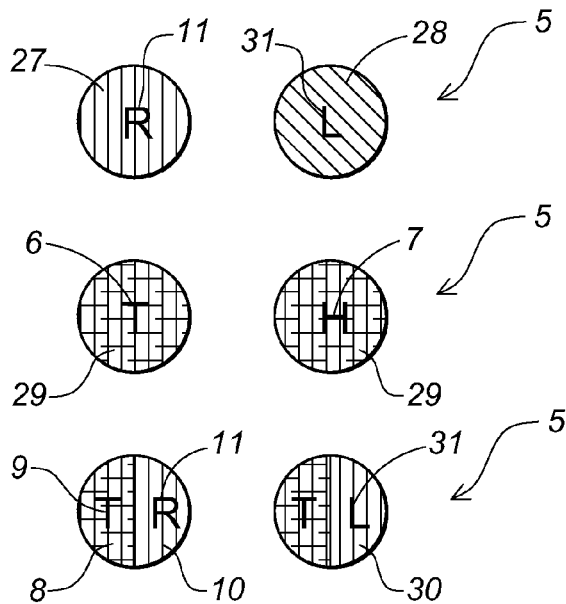
FIG. 3 depicts the magnets.
Figure 4:
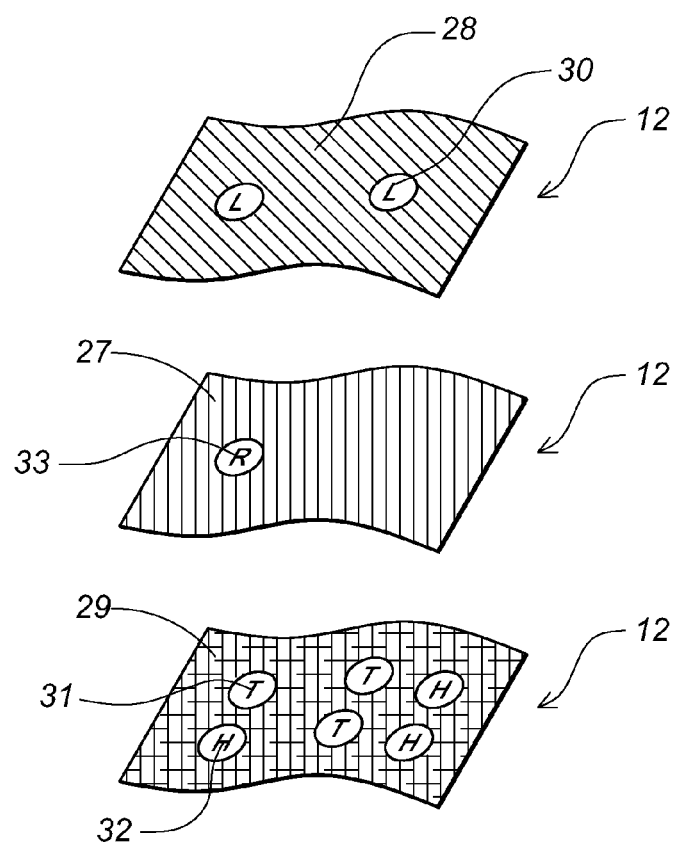
FIG. 4 depicts the surgical drapes.

The present invention relates to a method and apparatus for preventing surgical site errors. The apparatus includes a ferromagnetic, dry-erase whiteboard 1 having a pair of anatomical figures imprinted adjacent to a side thereof. One of the FIG. 2 represents the human posterior while the other 3 represents the anterior. Adjacent to the anatomical figures is a text space 4 for writing a description 25 of a planned surgical procedure and any additional pertinent patient information 26.

The apparatus further includes a plurality of color-coded magnets 5 for securing to representative locations on the anatomical figures. Each magnet has a specific color according to the area of the body requiring surgery. For example, red 27 may represent the right extremities, green 28 may represent the left extremities and gold 29 may represent the torso or head. In addition, the red magnets include the designation "R" 11, the green magnets include the designation "L" 31 while the gold magnets may further include the designation "T" 6 or "H" 7 to specify torso or head, respectively. Furthermore, to further identify the left torso and right torso, a number of the magnets may include two identifying colors; for example, in order to clearly identify the right torso, a magnet may have a gold segment 8 with the letter "T" 9 inscribed thereon and a red segment 10 with the letter "R" 11 inscribed thereon; to identify the left torso, a magnet may have a green segment 30 with the letter "L" 31 inscribed thereon.

The apparatus further includes a plurality of surgical drapes 12 each preferably colored green, red or gold to identify specific surgical locations as described above. Each drape includes an opening for exposing the proposed surgical site and a surgical site image imprinted thereon, such as L 30, T 31, H 32 or R 33 similar to those on the magnets.

The method of preventing surgical errors using the above-described apparatus includes a medical worker placing a color-coded magnet on one of the whiteboard anatomical figures; for example, if the surgical site is the right torso, the red and gold magnet is placed on the anatomical figure's right torso portion as depicted in FIG. 2. A medical worker then writes a description of the surgical procedure on the space adjacent to the figures using a colored marker(s) matching the magnet color(s). The colored markers preferably each include magnets on the shaft for adhering to the dry erase board. The appropriately-colored drape is positioned over the patient with the opening exposing the surgical site. At the time of surgery, a surgeon examines the whiteboard to identify the magnet's location, indicia and color, then reviews the written data content and color and finally examines the drape color and indicia. If all colors, text and indicia unanimously confirm a proposed surgical site per the criteria set forth above, surgery may safely begin; otherwise, the surgeon is alerted to investigate the discrepancy.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An apparatus for preventing surgical errors comprising:
    a ferromagnetic board having a pair of anatomical figures imprinted thereon, one of said figures representing a human posterior, a second of said figures representing a human anterior;
    a text space adjacent to said figures for writing a description of patient information and a planned surgical procedure;
    a plurality of color-coded magnets magnetically securable to a desired location on either of the anatomical figures, each of said magnets having a specific color that predefine an area of a patient's body requiring surgery,
    a plurality of surgical drapes, each of said drapes having a discrete color identical to at least one of said magnets for overlaying a patient to conspicuously identify a proposed surgical site.

2. The apparatus according to claim 1 wherein a predetermined number of said magnets are multi-colored to more narrowly define a proposed surgical site.

3. The apparatus according to claim 1 wherein each of said drapes includes an opening for exposing the proposed surgical site.

4. The apparatus according to claim 3 wherein each of said magnets includes identifying indicia thereon for identifying a proposed surgical site.

5. The apparatus according to claim 4 wherein each of said drapes have identifying indicia thereon for further identifying a proposed surgical site.

\* \* \* \* \*